US008048025B2

(12) United States Patent
Barenboym et al.

(10) Patent No.: US 8,048,025 B2
(45) Date of Patent: Nov. 1, 2011

(54) MULTI-PLANE MOTION CONTROL MECHANISM

(75) Inventors: Michael Barenboym, Framingham, MA (US); Isaac Ostrovsky, Wellesley, MA (US); Jozef Slanda, Milford, MA (US); Christopher Oskin, Grafton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 137 days.

(21) Appl. No.: 12/497,885

(22) Filed: Jul. 6, 2009

(65) Prior Publication Data

US 2010/0004591 A1    Jan. 7, 2010

Related U.S. Application Data

(60) Provisional application No. 61/078,656, filed on Jul. 7, 2008.

(51) Int. Cl.
  *A61M 31/00*   (2006.01)
(52) U.S. Cl. ...................... 604/95.04; 604/528
(58) Field of Classification Search ............... 604/95.04, 604/528
See application file for complete search history.

(56) References Cited

U.S. PATENT DOCUMENTS

| 4,566,437 A | 1/1986 | Yamaguchi |
| 4,617,915 A | 10/1986 | Arakawa |
| 4,998,916 A | 3/1991 | Hammerslag et al. |
| 5,060,660 A | 10/1991 | Gambale et al. |
| 5,281,214 A | 1/1994 | Wilkins et al. |
| 5,325,845 A * | 7/1994 | Adair .................. 600/114 |
| 5,347,989 A | 9/1994 | Monroe et al. |
| D351,652 S | 10/1994 | Thompson et al. |
| 5,352,237 A | 10/1994 | Rodak et al. |
| 5,413,107 A * | 5/1995 | Oakley et al. ............ 600/463 |
| 5,462,527 A * | 10/1995 | Stevens-Wright et al. ... 604/528 |
| 5,611,777 A | 3/1997 | Bowden et al. |
| 5,656,030 A | 8/1997 | Hunjan et al. |
| 5,667,476 A | 9/1997 | Frassica et al. |
| 5,702,349 A | 12/1997 | Morizumi |
| 5,860,953 A | 1/1999 | Snoke et al. |

(Continued)

FOREIGN PATENT DOCUMENTS

DE    26 03 370 A1    8/1977

(Continued)

OTHER PUBLICATIONS

International Search Report and Written Opinion for PCT/US07/11912, mailed on Sep. 12, 2008; 8 pages.

(Continued)

*Primary Examiner* — Nicholas D Lucchesi
*Assistant Examiner* — Gerald Landry, II
(74) *Attorney, Agent, or Firm* — Finnegan, Henderson, Farabow, Garrett & Dunner LLP

(57) ABSTRACT

A hand-holdable steering mechanism is used as part of a medical device such as a catheter or an endoscope to allow movement of a steerable distal portion of the catheter or endoscope. The mechanism can include a housing and an actuation system. The actuation system is adapted for one-handed operation by a user, and it allows the user to achieve 360 degree articulation of the steerable distal portion. The actuation system can include a first actuator and a second actuator where the first and second actuators are movable with respect to each other. The first actuator can be at least partially disposed within the second actuator.

20 Claims, 10 Drawing Sheets

U.S. PATENT DOCUMENTS

| | | | |
|---|---|---|---|
| 5,882,333 | A | 3/1999 | Schaer et al. |
| 5,897,529 | A | 4/1999 | Ponzi |
| 5,906,590 | A | 5/1999 | Hunjan et al. |
| 5,957,865 | A | 9/1999 | Backman et al. |
| 6,007,531 | A | 12/1999 | Snoke et al. |
| 6,027,473 | A | 2/2000 | Ponzi |
| 6,059,739 | A | 5/2000 | Baumann |
| 6,066,125 | A | 5/2000 | Webster, Jr. |
| 6,123,699 | A | 9/2000 | Webster, Jr. |
| 6,171,277 | B1 | 1/2001 | Ponzi |
| 6,183,435 | B1 | 2/2001 | Bumbalough et al. |
| 6,183,463 | B1 | 2/2001 | Webster, Jr. |
| 6,198,974 | B1 | 3/2001 | Webster, Jr. |
| 6,203,507 | B1 | 3/2001 | Wadsworth et al. |
| 6,267,746 | B1 | 7/2001 | Bumbalough |
| 6,468,260 | B1 | 10/2002 | Bumbalough et al. |
| 6,500,167 | B1 | 12/2002 | Webster, Jr. |
| 6,571,131 | B1 | 5/2003 | Nguyen |
| 6,605,086 | B2 | 8/2003 | Hayzelden et al. |
| 6,663,588 | B2 * | 12/2003 | DuBois et al. ............ 604/95.04 |
| 6,679,873 | B2 | 1/2004 | Rabiner et al. |
| 6,783,510 | B1 | 8/2004 | Gibson et al. |
| 6,802,835 | B2 | 10/2004 | Rabiner et al. |
| 6,837,867 | B2 | 1/2005 | Kortelling |
| 6,945,956 | B2 | 9/2005 | Waldhauser et al. |
| 6,966,906 | B2 | 11/2005 | Brown |
| 7,037,290 | B2 | 5/2006 | Gardeski et al. |
| 7,060,024 | B2 | 6/2006 | Long et al. |
| 7,060,025 | B2 | 6/2006 | Long et al. |
| 7,115,134 | B2 | 10/2006 | Chambers |
| 7,144,371 | B2 * | 12/2006 | Edwardsen et al. ......... 600/459 |
| 7,232,437 | B2 | 6/2007 | Berman et al. |
| 7,238,180 | B2 | 7/2007 | Mester et al. |
| 7,811,277 | B2 * | 10/2010 | Boulais ........................ 604/528 |
| 2003/0149422 | A1 * | 8/2003 | Muller .......................... 604/528 |
| 2004/0059191 | A1 | 3/2004 | Krupa et al. |
| 2004/0193239 | A1 | 9/2004 | Falwell et al. |
| 2005/0080476 | A1 | 4/2005 | Gunderson et al. |
| 2005/0256375 | A1 | 11/2005 | Freed |
| 2005/0277874 | A1 | 12/2005 | Selkee |
| 2005/0277875 | A1 | 12/2005 | Selkee |
| 2005/0288627 | A1 | 12/2005 | Mogul |
| 2006/0142694 | A1 | 6/2006 | Bednarek et al. |
| 2006/0173448 | A1 | 8/2006 | Scheller et al. |
| 2006/0252993 | A1 | 11/2006 | Freed et al. |
| 2007/0060878 | A1 * | 3/2007 | Bonnette et al. ........... 604/95.04 |
| 2007/0156116 | A1 | 7/2007 | Gonzalez |
| 2007/0203474 | A1 | 8/2007 | Ryan et al. |
| 2007/0219529 | A1 | 9/2007 | Abe et al. |
| 2007/0270647 | A1 | 11/2007 | Nahen et al. |
| 2007/0282167 | A1 | 12/2007 | Barenboym et al. |
| 2008/0051802 | A1 | 2/2008 | Schostek et al. |
| 2009/0171275 | A1 | 7/2009 | Ostrovsky et al. |
| 2009/0234280 | A1 * | 9/2009 | Tah et al. .................... 604/95.04 |
| 2009/0287188 | A1 * | 11/2009 | Golden et al. ................ 604/528 |

FOREIGN PATENT DOCUMENTS

| | | | |
|---|---|---|---|
| EP | 0 521 595 | B1 | 5/1999 |
| EP | 0 668 052 | B1 | 1/2003 |
| WO | WO 93/20878 | A | 10/1993 |
| WO | WO 2007/136754 | A2 | 11/2007 |
| WO | WO 2007/136829 | A1 | 11/2007 |

OTHER PUBLICATIONS

International Preliminary Report on Patentability for PCT/US07/11912, mailed in Dec. 4, 2008; 6 pages.

International Search Report and Written Opinion for PCT/US08/86142, mailed on Mar. 11, 2009; 10 pages.

International Search Report and Written Opinion for PCT/US09/34831, mailed on May 13, 2009; 13 pages.

International Search Report and Written Opinion for PCT/US09/48792, mailed on Sep. 22, 2009; 15 pages.

International Search Report and Written Opinion for PCT/US09/49809, mailed on Oct. 28, 2009; 10 pages.

* cited by examiner

MULTI-PLANE MOTION CONTROL MECHANISM

CROSS-REFERENCE TO RELATED APPLICATIONS

This application claims priority to and the benefit of Provisional U.S. Patent Application Ser. No. 61/078,656, filed Jul. 7, 2008, the entirety of which is incorporated herein by reference.

TECHNICAL FIELD

The invention generally relates to a mechanism for controlling articulation of a steerable portion of a medical device, and more particularly to a one-handed or one-fingered steering mechanism. The medical device controls articulation of the steerable portion on at least two planes so that 360 degree articulation of the steerable portion is achievable.

BACKGROUND INFORMATION

Steering mechanisms are used to steer or direct a medical instrument, for example a catheter or endoscope, to a desired position or location in a body of a patient. One known steering mechanism resembles a joystick. The configuration of the joystick usually includes a plate attached to control wires. The plate, however, must be large to accommodate the desired articulations of the steerable medical device. Additionally, the single control element encompassed in the joystick control mechanism makes the introduction of force leverage very difficult, especially in a procedure during which an increased leverage is needed for different articulation planes. Further, all control wires are manipulated by the joystick, therefore, movement of the joystick may cause additional, albeit unintended, articulation of the catheter or endoscope.

Another known steering mechanism includes multiple slidable buttons. Each button is connected to a puller wire so that when the button is moved, the puller wire moves the catheter in a single direction associated with the puller wire. Thus, at least four slidable buttons are required to achieve 360 degree articulation of the catheter or endoscope. The sliding motion of the buttons on this steering mechanism makes introduction of force leverage very difficult. Furthermore, the catheter can only be articulated along one plane at a time unless the user moves more than one button at the same time, which requires that the user either use multiple fingers or continuously move his or her hand to manipulate the buttons and operate the device.

SUMMARY OF THE INVENTION

It is an object of the invention to allow steering operation of a medical device by a single hand or a single finger of a user. A steering mechanism according to the invention can control 360 degree articulation of a steerable portion of a medical device. A steering mechanism according to the invention can articulate a steerable portion of a medical device along one plane without unintentionally affecting the articulation of the steerable portion along a different plane. A steering mechanism (or steerable medical device) according to the invention can also introduce force leverage, or other mechanical advantage, for articulating a steerable device (or steerable portion of the steerable medical device).

In one aspect, the invention relates to a steering mechanism for use as part of a medical device. The steering mechanism can comprise a housing and an actuation system. The housing can include a proximal end and a distal end. The housing can be couplable to a steerable medical device and can substantially extend along a longitudinal axis. The actuation system is adapted for one-handed operation by a user. The actuation system is configured to move at least a portion of the steerable medical device along a first plane and a second plane different than the first plane such that 360 degree articulation of the steerable medical device is achievable. The actuation system includes a first actuator and a second actuator. The first actuator can be movable with respect to the second actuator and to a second axis different than the longitudinal axis. The first actuator can be at least partially disposed within the second actuator. The second actuator can be coupled to the proximal end of the housing and can be movable with respect to the housing and to the longitudinal axis.

Embodiments according to this aspect of the invention can include various features. For example, the first actuator and the second actuator can be adapted for one-fingered operation by a user. The first actuator can be movable in a first direction and a second direction different than the first direction such that the first actuator can move at least a portion of the steerable medical device in a first direction and a second direction different than the first direction along the first plane as the first actuator is moved in its first direction and its second direction, respectively.

In another example, the second actuator can be movable in a first direction and a second direction different than the first direction such that the second actuator can move at least a portion of the steerable medical device in a first direction and a second direction different than the first direction along the second plane as the second actuator is moved in its first direction and its second direction, respectively. The second actuator can include a casing defining an interior cavity, and the first actuator can include a cam that is at least partially disposed within the interior cavity of the casing of the second actuator. The first actuator can include a lever portion configured to extend from the cam through an elongate opening defined by the casing of the second actuator.

In some embodiments, the cam of the first actuator is a first cam, and the second actuator includes a second cam at least partially disposed within the interior cavity of the casing of the second actuator. The first actuator can be movably coupled to the second actuator by a dowel pin.

In another example, the steering mechanism can further comprise a vertical plane wire coupled to and movable by the first actuator. At least one end of the vertical plane wire is couplable to the steerable medical device and the vertical plane wire can be configured to move at least a portion of the steerable medical device along the first plane when the vertical plane wire is moved by the first actuator. The steering mechanism can also further comprise a horizontal plane wire coupled to and movable by the second actuator. At least one end of the horizontal plane wire can be couplable to the steerable medical device and the horizontal plane wire can be configured to move at least a portion of the steerable medical device along the second plane when the horizontal plane wire is moved by the second actuator. The second actuator can include a cam configured to move the horizontal plane wire when the second actuator is moved in at least one of its first direction and its second direction.

In yet another example, the steering mechanism can further comprise a gear that is fixedly coupled to the housing and a cam that is included in the second actuator. The gear can be adapted to engage a portion of the second actuator as the second actuator is moved in at least one of the first direction and the second direction. The cam of the second actuator can be moved from a first position to a second position different than the first position, such as when the second actuator is moved in its first direction and as the portion of the second actuator engages the gear. A portion of the second actuator can include a first series of teeth in a circular configuration and the gear can include a second series of teeth configured to matingly engage the first series of teeth of the second actuator as the second actuator is moved in at least one of its first or second direction.

In another aspect, the invention generally involves a medical device that includes an elongated member and a steering mechanism. The elongated member includes a proximal end and a distal end and defines a lumen extending at least partially therethrough. The elongated member can include including a steerable portion. The elongated member can extend along a longitudinal axis when the elongated member is in a first position. The steering mechanism can be coupled to the elongated member and can be adapted to move the steerable portion of the elongated member along at least a first plane and a second plane different than the first plane. The steering mechanism can be adapted for one-handed operation by a user. The steering mechanism can include a first actuator adapted to move the steerable portion of the elongated member along the first plane and a second actuator adapted to move the steerable portion of the elongated member along the second plane. The first actuator can be movably coupled to the second actuator.

Embodiments according to this other aspect of the invention can include various features. For example, the first actuator and the second actuator can be adapted to achieve 360 degree articulation of the steerable portion of the elongated member with respect to the longitudinal axis. The first actuator can be at least partially disposed within a casing of the second actuator.

In another example, the steering mechanism can further comprise a housing including a proximal end and a distal end and defining an interior cavity extending at least partially therethrough. The distal end of the housing can be coupled to the proximal end of the elongated member, and the second actuator can be movably coupled to the proximal end of the housing. The second actuator can be selectively turnable in a first direction and a second direction different than the first direction around the longitudinal axis and with respect to the housing.

In another example, the steering mechanism can further comprise a gear and a cam included in the second actuator. The gear can be fixedly coupled to the housing. The gear can be adapted to engage a portion of the second actuator as the second actuator is actuated. The cam can be configured to move between a first position and a second position as the second actuator is actuated and as the portion of the second actuator engages the gear.

The steerable medical device can further comprise a vertical plane wire and a horizontal plane wire. The vertical plane wire can be coupled to the elongated member and to the first actuator. The vertical plane wire can be movable in a first direction and a second direction different than the first direction, such that when the first actuator is moved in its first direction the vertical plane wire moves in its first direction. The vertical plane wire can be configured to move the steerable portion of the elongated member in the first direction along the first plane when the vertical plane wire moves in its first direction. The horizontal plane wire can be coupled to the elongated member and to the second actuator. The horizontal plane wire can be movable in a first direction and a second direction different than the first direction, such that when the second actuator is moved in its first direction the horizontal plane wire moves in its first direction. The horizontal plane wire can be configured to move the steerable portion of the elongated member in the first direction along the second plane when the horizontal plane wire moves in its first direction.

In a further example, the vertical plane wire can be a first vertical plane wire, and the steerable medical device can further comprise a second vertical plane wire coupled to the elongated member and to the first actuator. The second vertical plane wire can be movable in a first direction and a second direction different than the first direction, such that when the first actuator is moved in its second direction the second vertical plane wire moves in its first direction. The second vertical plane wire can be configured to move the steerable portion of the elongated member in the second direction along the first plane when the second vertical plane wire moves in its first direction. The horizontal plane wire can be a first horizontal plane wire, and the steerable medical device can further comprise a second horizontal plane wire coupled to the elongated member and to the second actuator. The second horizontal plane wire can be movable in a first direction and a second direction different than the first direction, such that when the second actuator is moved in its second direction the second horizontal plane wire moves in its first direction. The second horizontal plane wire can be configured to move the steerable portion of the elongated member in the second direction along the second plane when the second horizontal plane wire moves in its first direction.

DESCRIPTION

Apparatuses for controlled articulation of a steerable device are described herein. For example, in some embodiments, the apparatus is a steering mechanism for use as part of a medical device. The steering mechanism can be used as part of or with a medical device including a steerable member, such as, for example, a catheter or endoscope. In some embodiments, the apparatus is a medical device that includes a steering mechanism.

Figure 1:
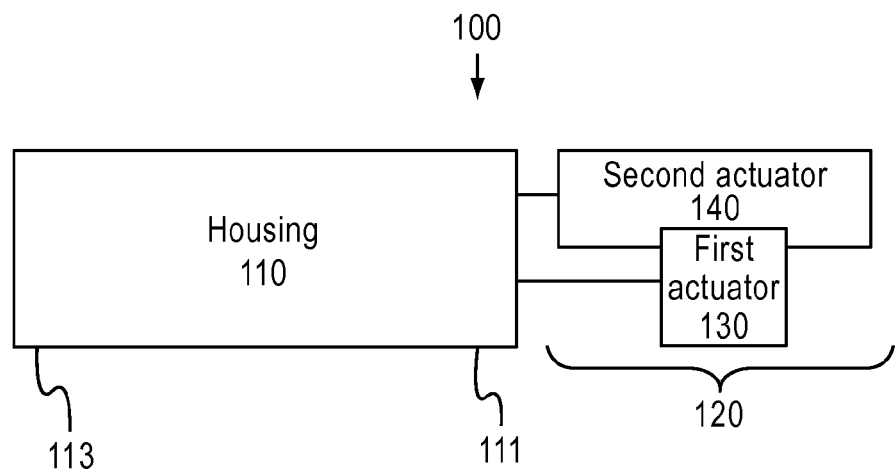
FIG. 1 is a schematic illustration of a steering mechanism for use with or as part of a medical device according to an embodiment of the invention.

In one embodiment, as schematically illustrated in FIG. 1, the apparatus 100 is a steering mechanism. The steering mechanism 100 is adapted to control articulation of a steerable portion of a device (also referred to herein as "steerable device") (not illustrated in FIG. 1).

The steering mechanism 100 includes a housing 110 and an actuation system 120. The housing 110 includes a proximal end 111 and a distal end 113. The housing 110 is couplable to the steerable device. In some embodiments, the distal end 113 of the housing 110 is couplable to the steerable device.

In some embodiments, the actuation system 120 is adapted to control articulation of the steerable device along a first plane and a second plane different than the first plane. In some embodiments, the steering mechanism 100 is adapted to move the steerable device along the first plane and the second plane such that 360 degree articulation of the steerable device is achievable.

The actuation system 120 includes a first actuator 130 and a second actuator 140. The first actuator 130 is movable with respect to the second actuator 140. In some embodiments, the first actuator 130 is at least partially disposed within the second actuator 140, as illustrated in FIG. 1.

The second actuator 140 is coupled to the housing 110. In the illustrated embodiment, the second actuator 140 is coupled to the proximal end 111 of the housing 110. The second actuator 140 is movable, or turnable, with respect to the housing 110.

The actuation system 120 is adapted for one-handed operation by a user. In some embodiments, the actuation system 120 is adapted for one-fingered operation by a user. For example, in some embodiments, the user can hold or lay the housing 110 of the steering mechanism in the user's hand and can actuate the actuation system 120 with a thumb or finger of the same hand. In another example, the user can grasp the housing 110 of the steering mechanism 110 and actuate at least one of the first or second actuators 130, 140 with a single thumb or finger without having to reposition his or her hand.

Figure 2:
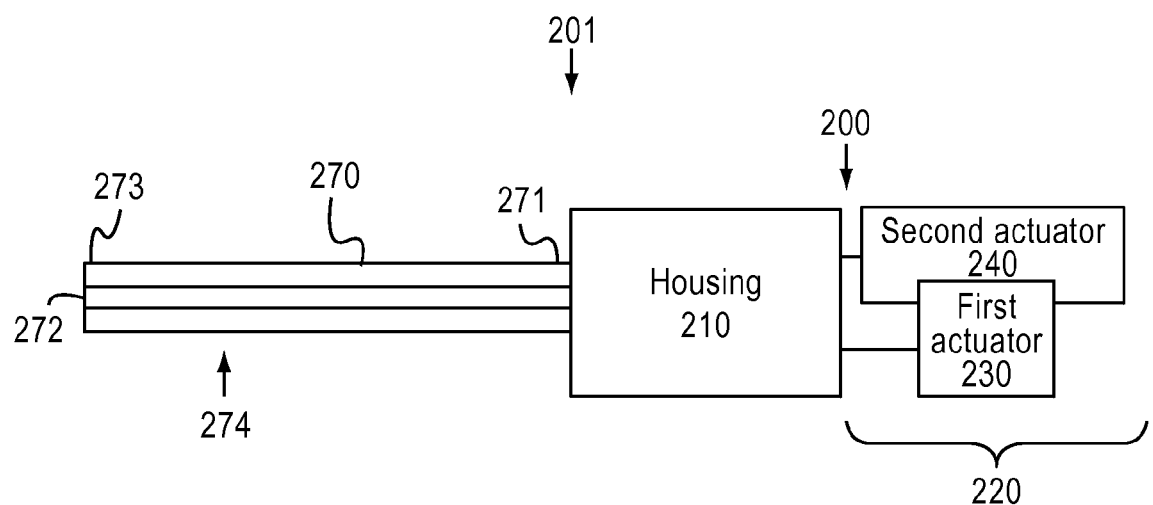
FIG. 2 is a schematic illustration of a steerable medical device according to an embodiment of the invention.

In some embodiments, as schematically illustrated in FIG. 2, the apparatus 201 is a steerable medical device. The steerable medical device 201 is adapted for controlled 360 degree articulation of a portion of the steerable medical device by manipulating another portion of the steerable medical device.

The steerable medical device 201 includes an elongated member 270 and a steering mechanism 200. The elongated member 270 includes a proximal end 271 and a distal end 273 and defines a lumen 272 extending at least partially therethrough. The elongated member 270 includes a steerable portion 274. In the illustrated embodiment, a portion of the elongated member 273 nearest the distal end 273 of the elongated member 273 is the steerable portion 274. In some embodiments, for example, the elongated member 270 is a catheter or endoscope.

As illustrated, the steering mechanism 200 is coupled to the elongated member 270. The steering mechanism 200 includes substantially similar embodiments as those described above with respect to steering mechanisms 100.

In some embodiments, the steering mechanism 200 is adapted for at least one of one-handed or one-fingered operation by a user. Said another way, a user can manipulate or control articulation of the steerable portion 274 of the elongated member 270 by controlling the steering mechanism 200 with a single hand or finger. The steering mechanism 200 is adapted to move the steerable portion 274 of the elongated member 270 along at least a first plane and a second plane different than the first plane.

The steering mechanism 200 includes a first actuator 230 and a second actuator 240. In some embodiments, the first actuator 230 is movably coupled to the second actuator 240. In the illustrated embodiment, the first actuator 230 is partially disposed within the second actuator 240. The first actuator 230 is adapted to move the steerable portion 274 of the elongated member 270 along the first plane. The second actuator 240 is configured to move the steerable portion 274 of the elongated member 270 along the second plane.

A steerable medical device 301 according to an embodiment of the invention is illustrated in FIGS. 3-10. The steerable medical device 301 is configured for controlled articulation of a portion of the device, such as for navigating pathways in a body of a patient. The steerable medical device 301 includes an elongated member 370 and a steering mechanism 300.

Figure 3:
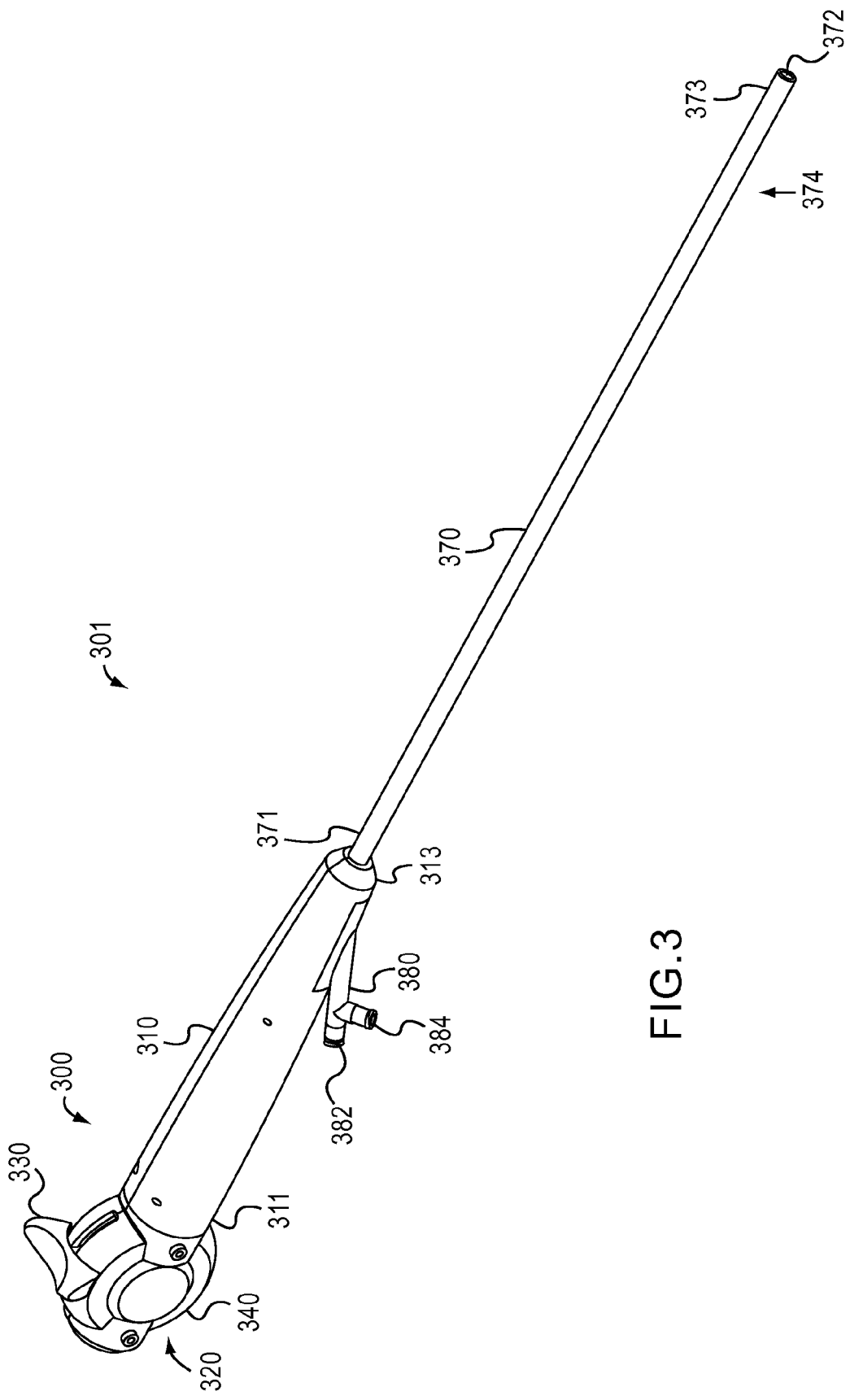
FIG. 3 is a perspective view of a steerable medical device according to an embodiment of the invention.

The elongated member 370 includes a proximal end 371 and a distal end 373 and defines a lumen 372 extending at least partially therethrough, as illustrated in FIG. 3. At least a portion 374 of the elongated member 370 is steerable. In some embodiments, for example, the elongated member 370 is a steerable catheter or endoscope.

Figure 9A:
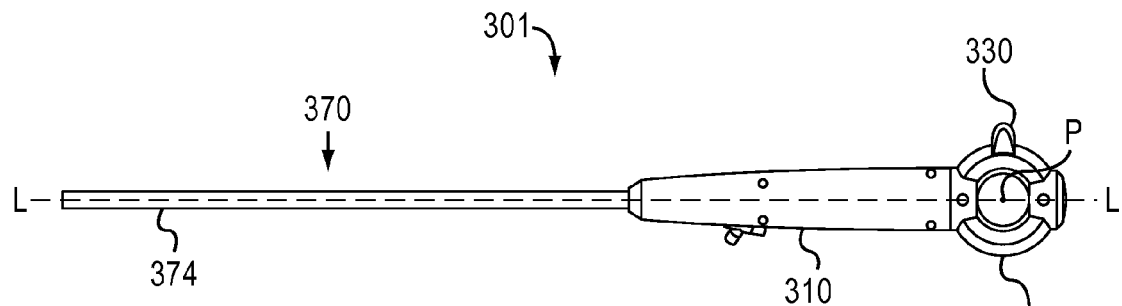
FIGS. 9A-9C are side views of the steerable medical device of FIG. 3 in a first, second, and third position, respectively.

The steerable medical device 301 substantially extends along a longitudinal axis L (illustrated in FIG. 9A). The elongated member 370 extends along the longitudinal axis L when the elongated member is in a first (or non-articulated or relaxed) position. In some embodiments, the elongated member 370 is biased towards the first (or non-articulated or relaxed) position. The steerable portion 374 of the elongated member 370 is adapted to articulate 360 degrees with respect to the longitudinal axis L.

The steering mechanism 300 of the steerable medical device 301 is illustrated in FIGS. 4-7. The steering mechanism 300 is adapted to control articulation of the steerable portion 374 of the device 301. The steering mechanism 300 is couplable to the elongated member 370.

Figure 4:
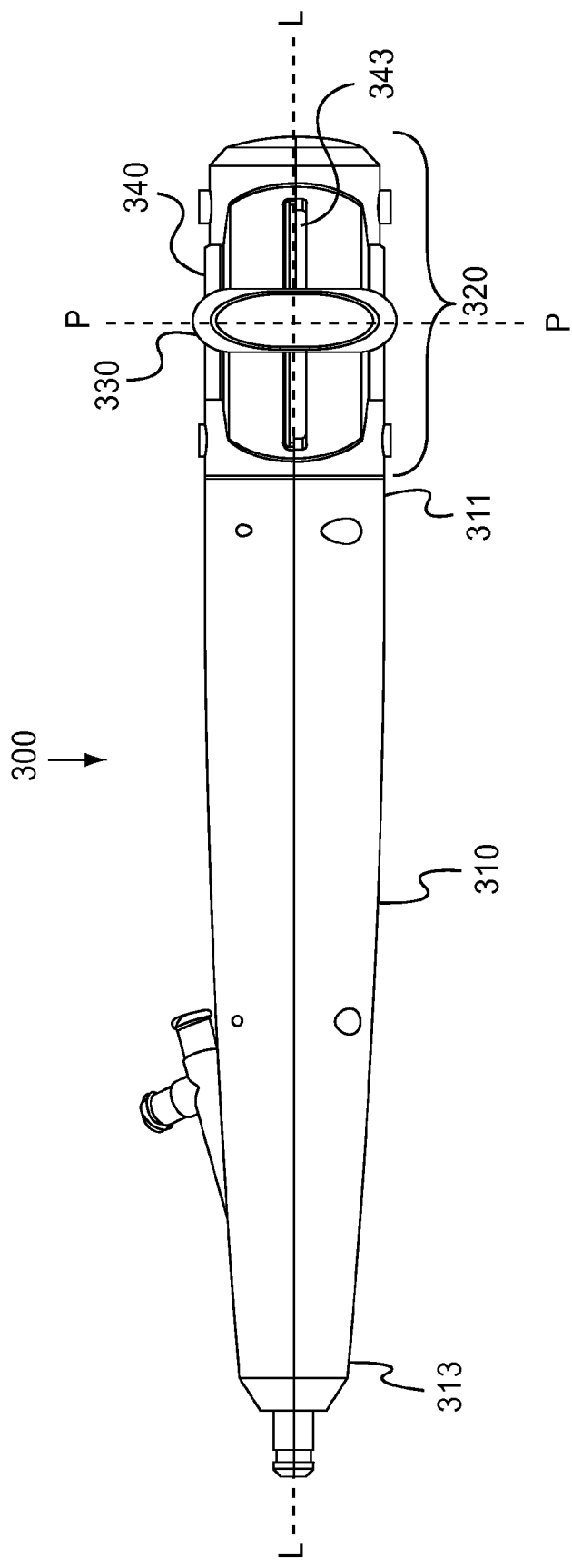
FIG. 4 is a top view of a steering mechanism of the steerable medical device of FIG. 3.

The steering mechanism 300 includes a housing 310 and an actuation system 320. The housing 310 includes a proximal end 311 and a distal end 313 and defines an interior cavity 315 extending at least partially therethrough. In some embodiments, the housing 310 is couplable to the elongated member 370. For example, in the illustrated embodiment, the distal end 313 of the housing 310 is configured to be coupled to the elongated member 370. The housing 310 substantially extends along the longitudinal axis L, as illustrated in FIG. 4.

Figure 5:
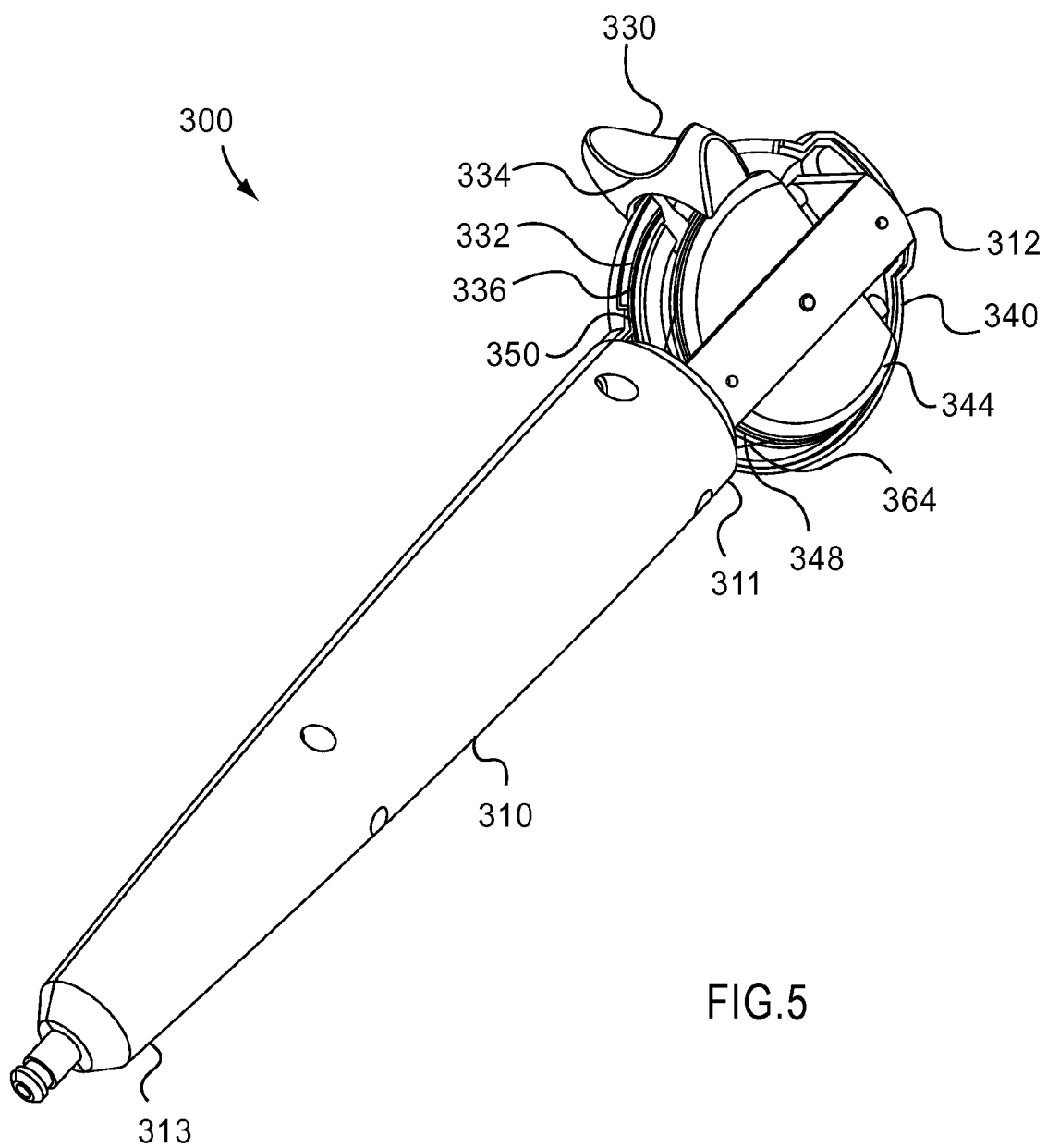
FIG. 5 is a perspective view of the steering mechanism of the steerable medical device of FIG. 3 with a portion of the steering mechanism removed.

As illustrated in FIG. 5, in some embodiments, the actuation system 320 is coupled to the housing 310 by a coupler 312. In the illustrated embodiment, the actuation system 320 is coupled to the proximal end 311 of the housing 310.

The actuation system 320 is configured to move at least a portion of the elongated member 370, such as the steerable portion 374. In some embodiments, the actuation system 320 is configured to move the steerable portion 374 of the elongated member 370 along a first plane and a second plane different than the first plane such that 360 degree articulation of the steerable portion of the elongated member is achievable.

The actuation system 320 includes a first actuator 330 and a second actuator 340. The first actuator 330 and the second actuator 340 are adapted to achieve 360 degree articulation of the steerable portion 374 of the elongated member 370 with respect to the longitudinal axis L.

The first actuator 330 is adapted to move the elongated member 370 of the device along the first plane when the first actuator 330 is actuated (or moved) by a user. In some embodiments, the first plane is a vertical plane.

The first actuator 330 is configured to move between a first (or relaxed) position (illustrated in FIG. 9A) and a second position different than the first position (illustrated in FIG.

9B). In some embodiments, the first actuator 330 is configured to move to a third position different than the first and second positions (illustrated in FIG. 9C). When the housing 310 of the steering mechanism 300 is coupled to the elongate member 370 of the device 301, the first actuator 330 is configured to move the elongate member along the first plane when the first actuator is moved between its first position, its second position, and/or its third position.

Figure 6:
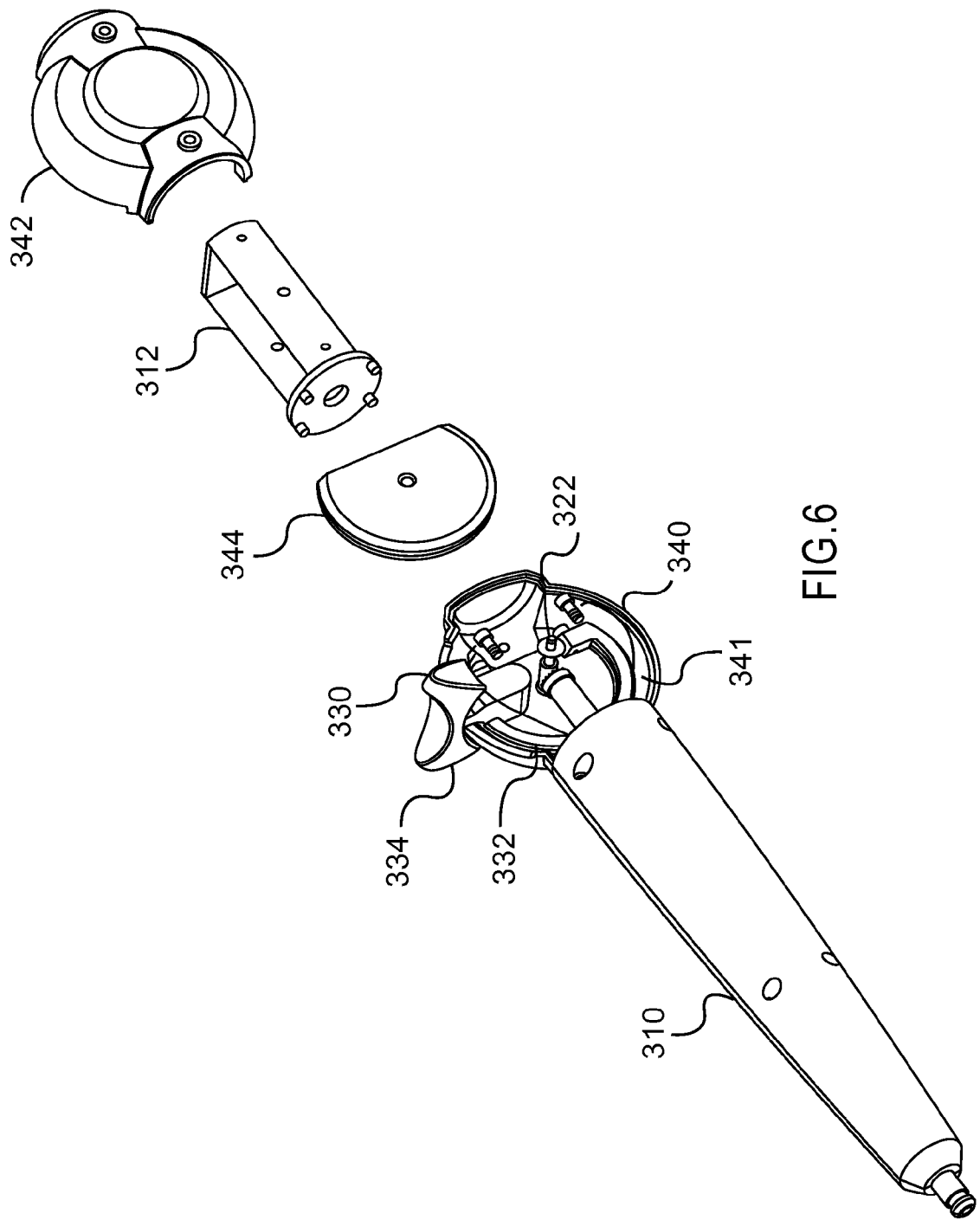
FIG. 6 is an exploded perspective view of the steering mechanism of the steerable medical device of FIG. 3.

The first actuator 330 is at least partially disposed within the second actuator 340. For example, as illustrated in FIGS. 5 and 6, the first actuator 330 includes a cam (also referred to herein as "first cam") 332 and a lever portion 334. The first cam 332 is at least partially disposed within the second actuator 340, as described below.

In some embodiments, the first actuator 330 is movably coupled to the second actuator 340. For example, as illustrated in FIG. 6, the first actuator 330 is coupled to the second actuator 340 by a dowel pin 322. At least a first portion of the dowel pin 322 is couplable to the first actuator 330 and at least a second portion of the dowel pin is couplable to the second actuator 340. In the illustrated embodiment, the first portion of the dowel pin 322 is disposed in a center portion of the first cam 332 of the first actuator 330. In some embodiments, the first cam 332 is movable with respect to the dowel pin 322. In the illustrated embodiment, the second portion of the dowel pin is disposed on a portion of the second actuator 340. In some embodiments, at least a portion of the second actuator 340 is movable with respect to the dowel pin 322.

The lever portion 334 of the first actuator 330 extends or protrudes from the first cam 332 through an elongate opening 343 defined by the second actuator 340 to an area accessible to a user. For example, in the illustrated embodiment, the lever portion 334 extends from the first cam 332 to an area outside the second actuator 340. The lever portion 334 of the first actuator 330 is configured to be moved by a user to actuate (or move) the first actuator.

Figure 11:
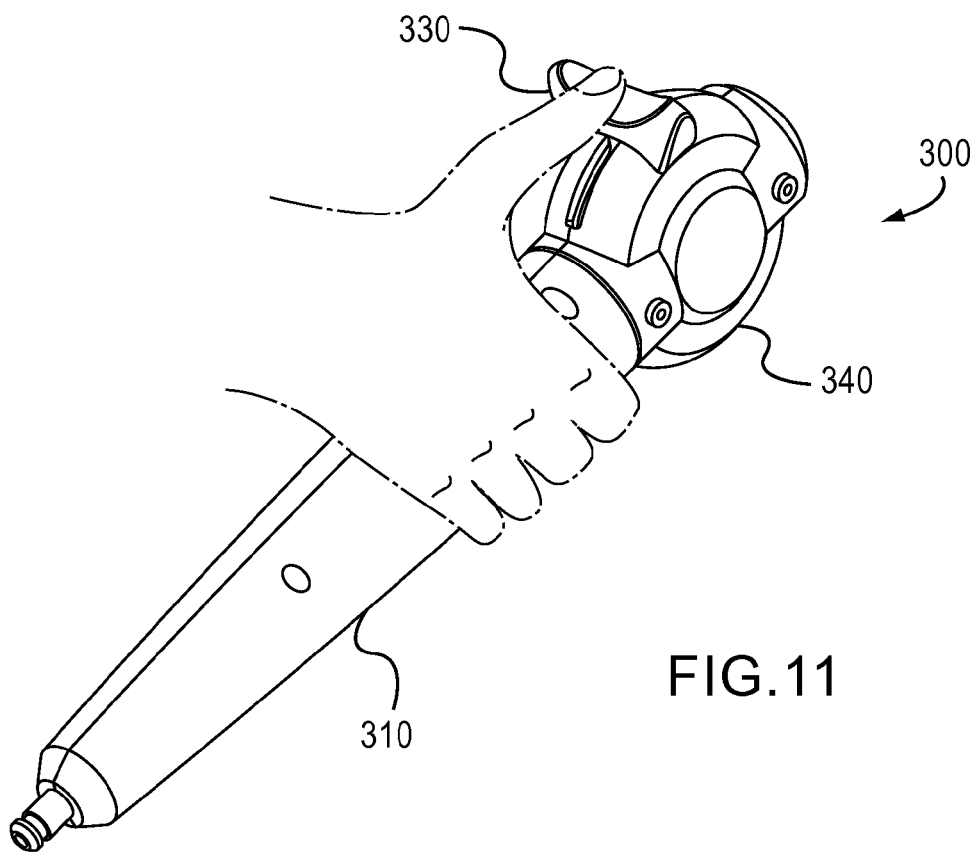
FIGS. 11 and 12 are perspective views of the steering mechanism of the steerable medical device of FIG. 3 being held by a hand of a user.
Figure 12:
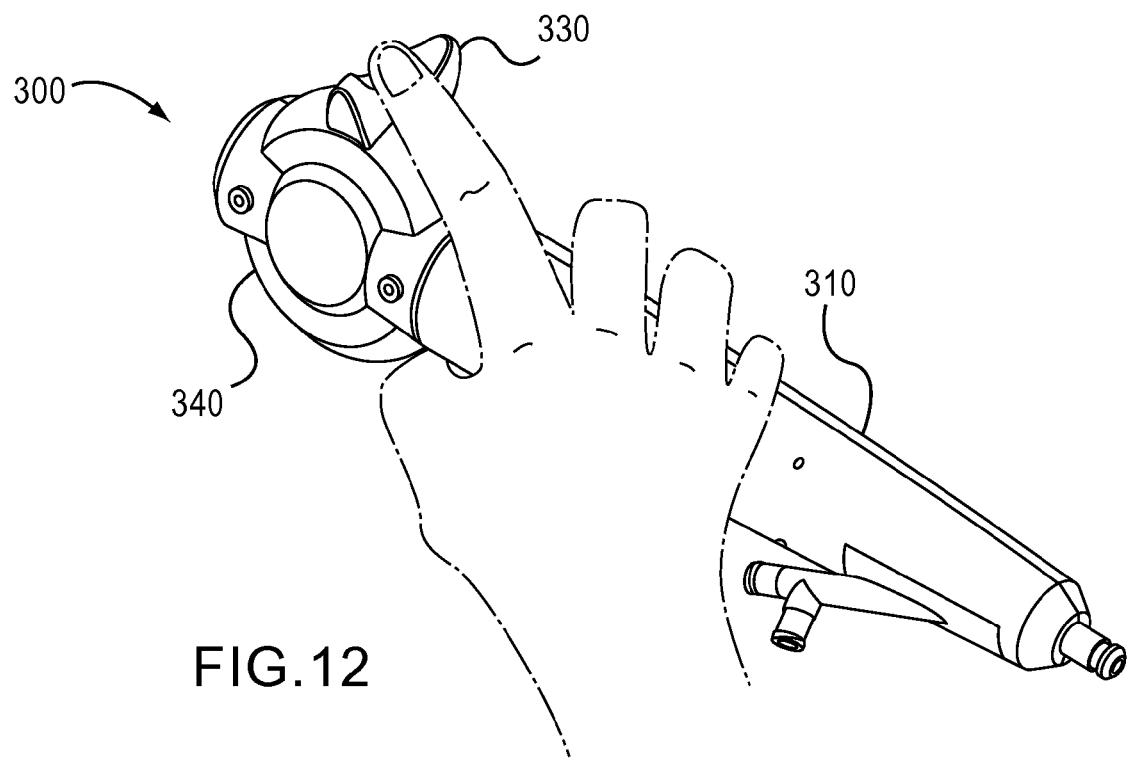

In the illustrated embodiment, the lever portion 334 of the first actuator 330 is contoured. A contoured configuration permits a user to rest a thumb or finger within the contour during operation of the steering mechanism, as illustrated in FIGS. 11 and 12. Although the lever portion 334 is illustrated as defining a curved contour, in other embodiments, the lever portion can have a different shape or contour, such as a straight or circular contoured portion. A user can increase the amount of force leverage introduced to the device 301, for example, by shifting his or her thumb or finger from the middle of the curved contour of the first actuator 330 to a further edge of the curve of the first actuator 330.

The first cam 332 is configured to move in response to movement of the first actuator 330. The first cam 332 is movable between at least a first position and a second position different than the first position. In some embodiments, the first cam 332 is movable to a third position different than the first and second positions, as described in more detail below.

Figure 8:
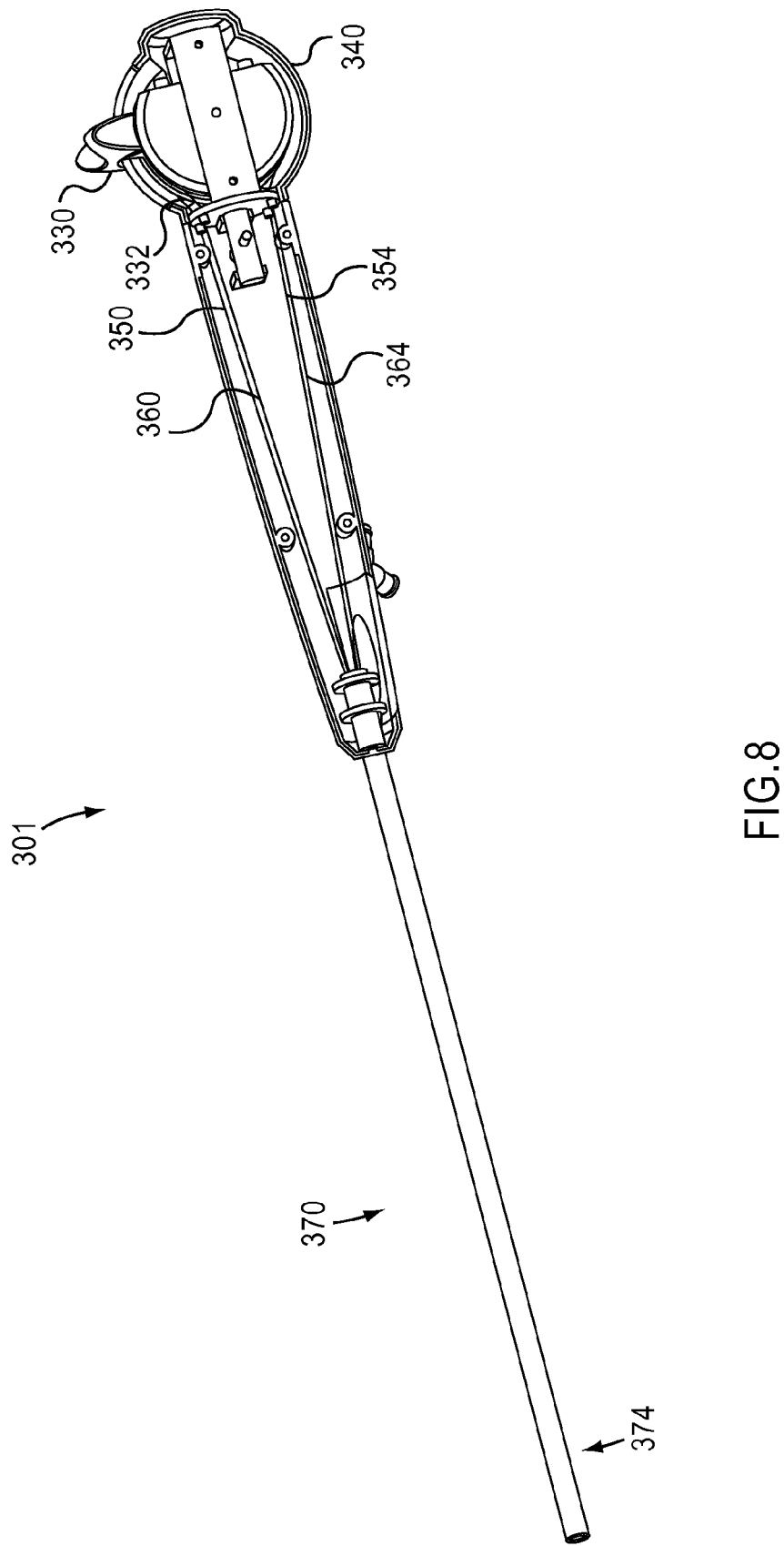
FIG. 8 is a perspective view of the steerable medical device of FIG. 3 with a portion of the steering mechanism removed.

As illustrated in FIG. 8, the steerable medical device 301 includes a first vertical plane wire 350 and a second vertical plane wire 354. The vertical plane wires 350, 354 are adapted to move the steerable portion 374 of the elongated member 370 along the first plane, as described in more detail below. The first vertical plane wire 350 is coupled to the elongated member 370 and to the first actuator 330. The first vertical plane wire 350 includes a first end and a second end (not illustrated). The first end of the first vertical plane wire 350 is coupled to the first cam 332 of the first actuator 330. The second end of the first vertical plane wire 350 is coupled to the elongated member 370.

The second vertical plane wire 354 is coupled to the elongated member 370 and to the first actuator 330. The second vertical plane wire 354 includes a first end and a second end (not illustrated). The first end of the second vertical plane wire 354 is coupled to the first cam 332 of the first actuator 330. The second end of the second vertical plane wire 354 is coupled to the elongated member 370.

As illustrated in FIG. 5, in some embodiments, the first cam 332 defines at least one groove 336. The groove 336 is configured to receive a portion of at least one of the vertical plane wires 350, 354. In the illustrated embodiment, a portion of the first vertical plane wire 350 is received in the groove 336.

Although the first cam 332 is illustrated and described as defining a groove 336, in other embodiments, the first cam is otherwise configured to engage the first or second vertical plane wires 350, 354. For example, in some embodiments, the first cam defines an opening configured to receive a portion of the first or second vertical plane wires 350, 354.

Figure 9B:
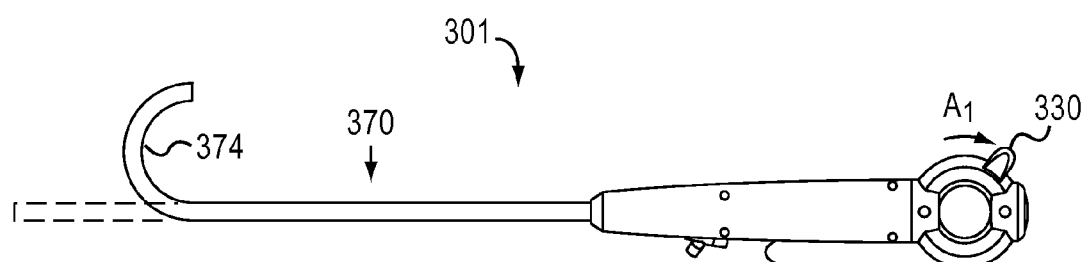
Figure 9C:
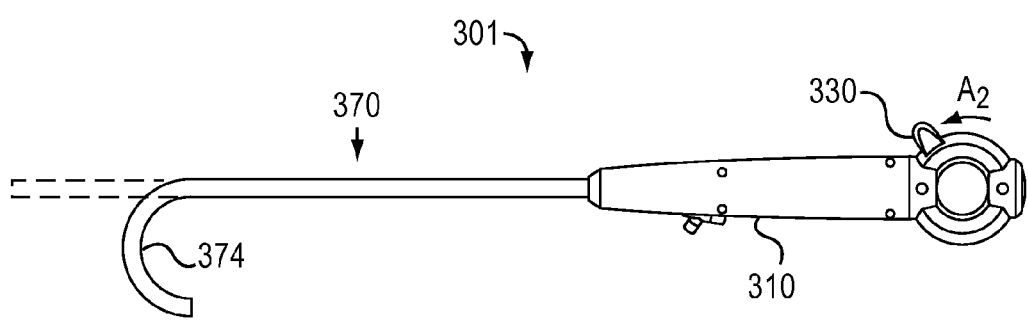

The first actuator 330 is adapted to move the steerable portion 374 of the elongated member 370 along the first plane, as illustrated in FIGS. 9A-9C. The first actuator 330 is movable in a first direction and a second direction different than the first direction.

The first actuator 330 is configured to move at least a portion of the elongated member 370 in a first direction as the first actuator is moved in its first direction, such as when moving the first actuator from its first position to its second position. As the first actuator is moved in its first direction (indicated by arrow $A_1$ in FIG. 9B), the first cam 332 correspondingly moves from its first position to or towards its second position.

As the first cam 332 moves towards its second position, the first cam moves the first vertical plane wire 350 in a first direction. Said another way, because the first vertical plane wire 350 is coupled to the first cam 332, movement of the first cam 332 to or towards its second position causes the first cam to pull on the first vertical plane wire, and thus moves the first vertical plane wire in its first direction. Movement of the first vertical plane wire 350 in its first direction moves (or bends or articulates) the steerable portion 374 of the elongated member 370 in the first direction, as illustrated in FIG. 9B.

The first actuator 330 is configured to move the at least a portion of the elongated member 370 in a second direction different than (or opposite to) the first direction as the first actuator is moved in its second direction, such as when moving the first actuator from its second position to its first position. As the first actuator 330 is moved in a second direction (indicated by arrow $A_2$ in FIG. 9C), the first cam 332 moves (or returns) from its second position to or towards its first position. If the user continues moving the first actuator 330 in the second direction, such as from its first position to or towards its third position, after the first cam 332 returns to its first position, the first cam 332 moves to or towards its third position.

As the first cam 332 moves to or towards its third position (or towards its first position from its second position), the second vertical plane wire 354 moves in a first direction. Said another way, because the second vertical plane wire 354 is coupled to the first cam 332, movement of the first cam 332 to or towards its third position causes the first cam to pull on the second vertical plane wire, and thus moves the second vertical plane wire in its first direction. In some embodiments, as the second vertical plane wire 354 moves in its first direction, the first vertical plane wire 350 moves in a second direction different than (or opposite to) its first direction.

Movement of the second vertical plane wire 354 in its first direction moves the steerable portion 374 of the elongated member 370 along the first plane in a second direction different than (or opposite to) the first direction, as illustrated in FIG. 9C. In some embodiments, the second vertical plane wire 354 is movable in a second direction different than (or opposite to) the first direction, such as when the first vertical plane wire is moved in its first direction.

Thus, movement of the first actuator 330 controls bi-directional articulation of the steerable portion 374 of the elongated member 370 along the first plane. Although the first plane is illustrated and described as being a vertical plane, in other embodiments, the first plane can be a different plane.

In FIGS. 9B and 9C, the elongated member 370 of the device 301 is illustrated in an articulated position, with the non-articulated (or relaxed) position of the elongated member illustrated in broken lines. The illustrations in FIGS. 9A-9C are representative only, and are not drawn to scale. For example, in some embodiments, the elongated (or steerable) member is a catheter or endoscope of greater length (such as compared to the length of the steering mechanism) than the elongated member in the illustrated embodiments.

In some embodiments, the first actuator 330 is movable with respect to a second axis P different than the longitudinal axis L along which the housing 310 extends. For example, in some embodiments, the first actuator is movable with respect to a second axis P (illustrated in FIGS. 4 and 9A) that is perpendicular (or orthogonal) to the longitudinal axis L. Because the first actuator 330 is moved or actuated with respect to the second axis P, for example as opposed to being moved linearly, the first actuator is adapted to introduce a mechanical advantage, e.g., force leverage, to the steerable device. In some embodiments, movement of the first actuator 330 and the first cam 332 introduced motion with force leverage directly onto the vertical plane wires 350, 354. In other embodiments, the first actuator 330 is configured to move linearly, such as a sliding actuator.

Although the steerable medical device 301 is described and illustrated herein as including first and second vertical plane wires 350, 354, in other embodiments, the steerable medical device includes a different number of vertical plane wires. For example, in some embodiments, the steerable medical device includes a single vertical plane wire. In such an embodiment, the first end and the second end of the vertical plane wire are each coupled to the elongated member of the steerable portion of the device. A portion of the vertical plane wire between the first end and the second end is coupled to or engaged with the first cam. For example, the vertical plane wire can extend from its first end coupled to the elongated member through the interior cavity of the housing, a middle portion of the vertical plane wire can be wrapped around or coupled to the first cam, and the vertical plane wire can extend back through the interior cavity of the housing to the second end coupled to the elongated member. In still other embodiments, the steerable medical device includes three, four, or more vertical plane wires.

As illustrated in FIGS. 3-10, actuation system 320 of the steering mechanism 300 includes a second actuator 340. The second actuator 340 is adapted to move the elongated member 370 along the second plane when the second actuator is actuated (or moved) by a user. In some embodiments, the second plane is a horizontal plane.

Figure 10A:
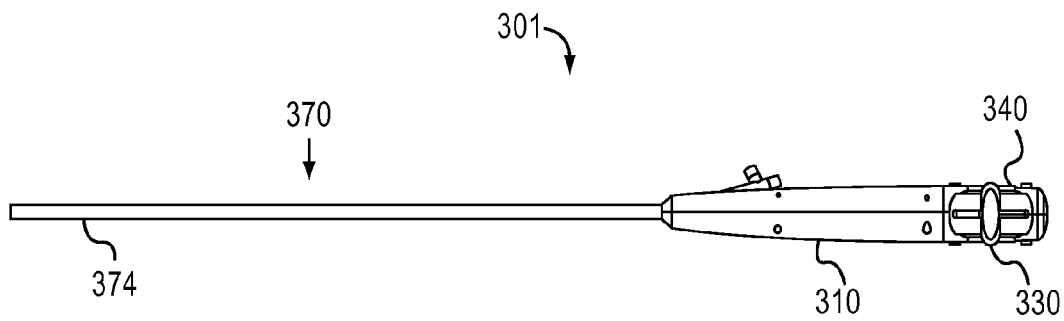
FIGS. 10A-10C are top views of the steerable medical device of FIG. 3 in a first, second, and third position, respectively.
Figure 10B:
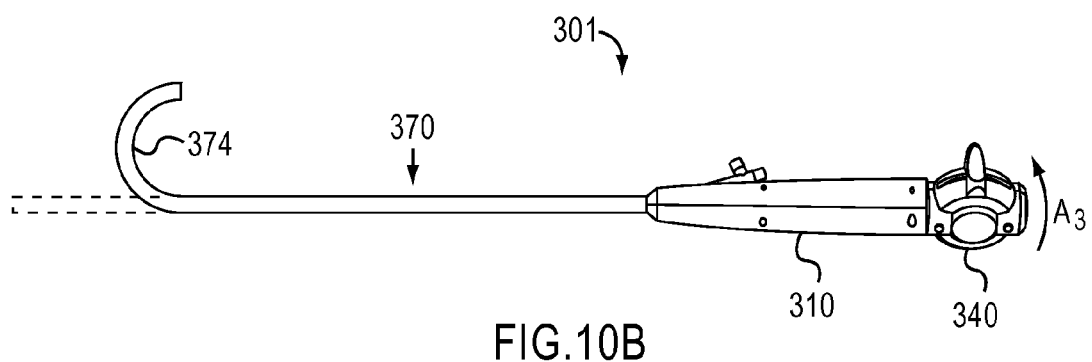

The second actuator 340 is configured to move between a first (or relaxed) position (illustrated in FIG. 10A) and a second position different than the first position (illustrated in FIG. 10B). In some embodiments, the second actuator 340 is configured to move to a third position different than the first and second positions (illustrated in FIG. 10C). When the housing 310 of the steering mechanism 300 is coupled to the elongate member 370 of the device 301, the second actuator 340 is configured to move the steerable member along the second plane when the second actuator is moved between its first position, its second position, and/or its third position.

In some embodiments, the second actuator 340 includes a casing 342 and a cam 344 (also referred to herein as the "second cam"). The casing 342 of the second actuator 340 defines an interior cavity 341 and an elongate opening 343.

In some embodiments in which the first actuator 330 is at least partially disposed within the second actuator 340, the first cam 332 is at least partially disposed within the interior cavity 341 of casing 342 of the second actuator. In such embodiments, the lever portion 334 of the first actuator 330 extends from the first cam 332 through the elongate opening 343 to an area outside the casing 342 of the second actuator 340. In other embodiments, the lever portion 334 of the first actuator 330 is accessible through the elongate opening 343 of the second actuator 340.

The second cam 344 of the second actuator 340 is at least partially disposed within the interior cavity 341 of the casing 342 of the second actuator. The second cam 344 is movable in response to movement of the second actuator 340. The second cam 344 is movable between at least a first position and a second position different than the first position. In some embodiments, the second cam 344 is movable to a third position different than the first and second positions, as described in more detail below. In some embodiments in which the second actuator 340 is movably coupled to the first actuator 330 by a dowel pin 322, the second portion of the dowel pin can be disposed in or coupled to a center portion of the second cam 344. The second cam 344 is movably coupled to the dowel pin 322.

Figure 7:
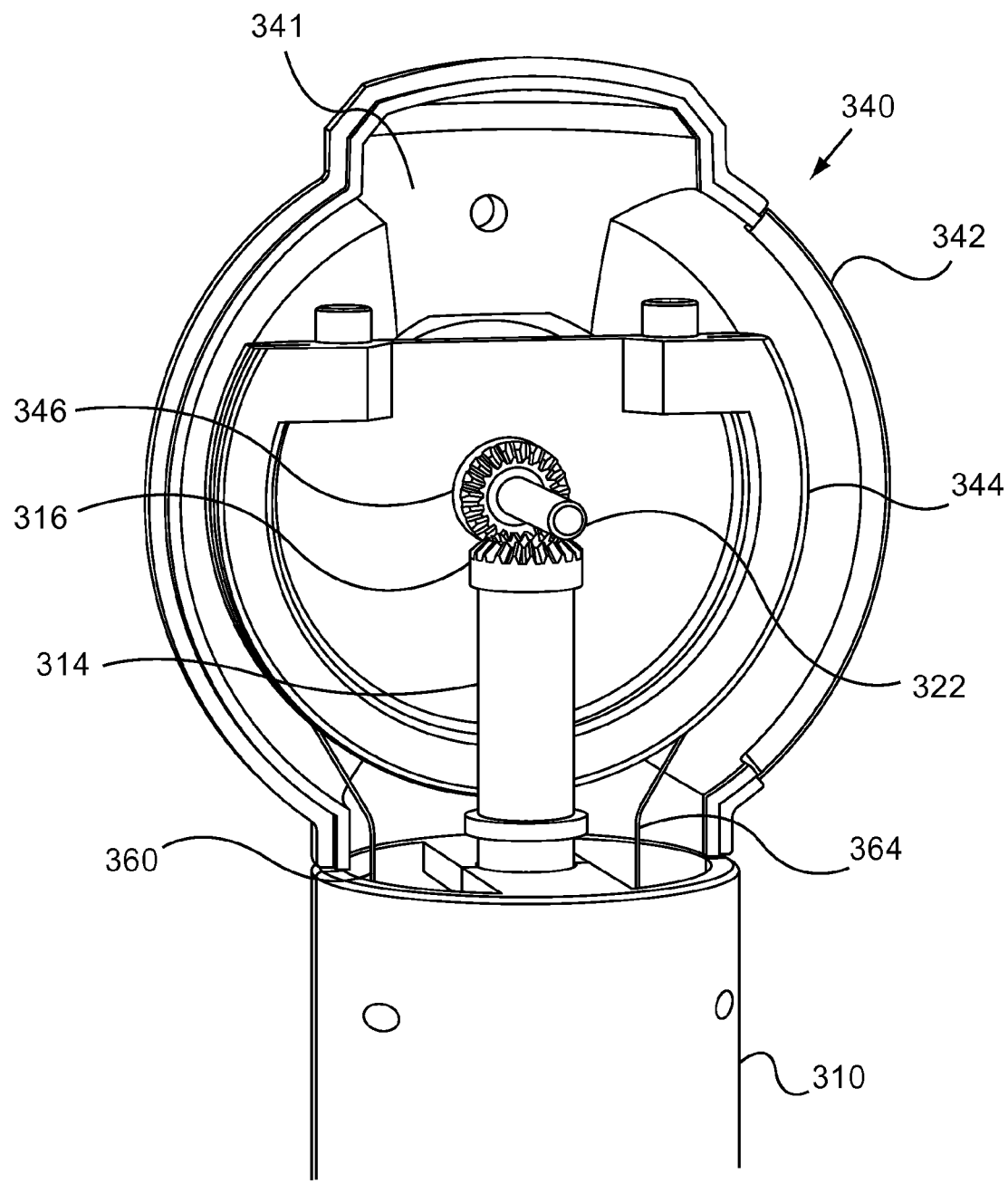
FIG. 7 is an enlarged view of a portion of the steering mechanism of the steerable medical device of FIG. 3.

In some embodiments, at least a portion of the second actuator 340 is adapted to engage a gear 314 included in the steering mechanism 300, as described in more detail below. For example, as illustrated in FIG. 7, a portion of the second actuator 340 includes a first series of teeth 346. In some embodiments, the first series of teeth 346 is coupled to or disposed on the second cam 344 of the second actuator 340. The first series of teeth 346 is arranged in a circular configuration. The first series of teeth 346 is adapted to engage the gear 314.

The gear 314 is fixedly coupled to the housing 310. In some embodiments, the gear 314 is fixedly coupled to the housing via the coupler 312. In the illustrated embodiment, the gear 314 extends from the interior cavity 315 of the housing 310 through an opening defined by the coupler 312 into a portion of the steering mechanism 300.

The gear 314 is adapted to engage a portion of the second actuator 340 as the second actuator is actuated. In some embodiments, the gear 314 includes a second series of teeth, illustrated in FIG. 7, configured to matingly engage the first series of teeth 346 disposed on the second actuator 340, as described in detail below.

The steerable medical device 301 includes a first horizontal plane wire 360 and a second horizontal plane wire 364. The horizontal plane wires 360, 364 are adapted to move the steerable portion 374 of the elongated member 370 along the second plane, as described in more detail below. The first horizontal plane wire 360 is coupled to the elongated member 370 and to the second actuator 340. The first horizontal plane wire 360 includes a first end and a second end (not illustrated). The first end of the first horizontal plane wire 360 is coupled to the second cam 344 of the second actuator 340. The second end of the first horizontal plane wire 360 is coupled to the elongated member 370.

The second horizontal plane wire 364 is coupled to the elongated member 370 and to the second actuator 340. The second horizontal plane wire 364 includes a first end and a second end (not illustrated). The first end of the second horizontal plane wire 364 is coupled to the second cam 344 of the second actuator 340. The second end of the second horizontal plane wire 364 is coupled to the elongated member 370.

As illustrated in FIG. 5, in some embodiments, the second cam 344 defines at least one groove 348 configured to receive a portion of at least one of the horizontal plane wires 360, 364. In the illustrated embodiment, the groove 348 is receiving a portion of the second horizontal plane wire 364.

Although the second cam 344 is illustrated and described as defining a groove 348, in other embodiments, the second cam is otherwise configured to engage the first or second horizontal plane wires 360, 364. For example, in some embodiments, the second cam defines an opening configured to receive a portion of the first or second horizontal plane wires 360, 364.

Figure 10C:
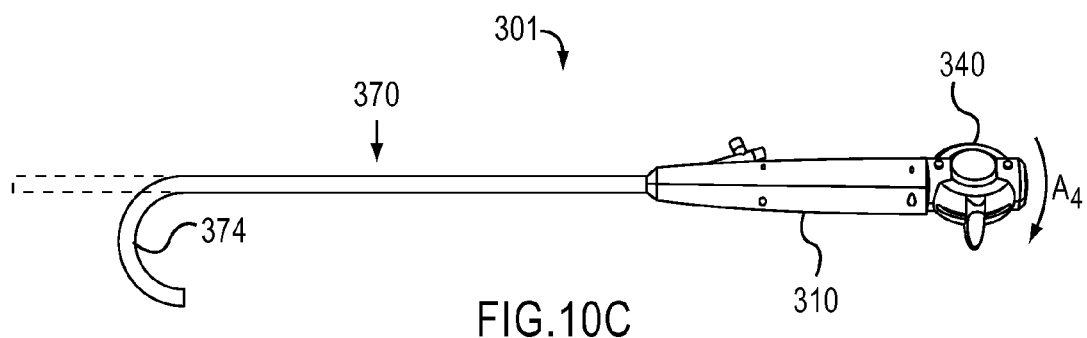

The second actuator 340 is adapted to move the steerable portion 374 of the elongated member 370 along the second plane when the second actuator is actuated (or moved) by a user, as illustrated in FIGS. 10A-10C. The second actuator 340 is selectively movable with respect to the longitudinal axis L. In some embodiments, the second actuator 340 is turnable and has longitudinal axis L as the pivoting point. The movement of the second actuator 340 with respect to the longitudinal axis L introduces motion to the device 301 with a mechanical advantage, e.g. force leverage.

The second actuator 340 is movable with respect to the housing 310. As the second actuator 340 is moved in at least one of a first direction or a second direction different than the first direction, the second actuator turns or swivels with respect to the housing. As the second actuator 340 moves or turns with respect to the housing, the second actuator also turns with respect to the longitudinal axis L.

The second actuator 340 is configured to move the at least a portion of the elongated member 370 in a first direction along the second plane as the second actuator is moved in its first direction, such as when the second actuator is moved from its first position to its second position. As the second actuator 340 is turned in the first direction (indicated by arrow $A_3$ in FIG. 10B), the first series of teeth 346 disposed on the second cam 344 move (or turn) in a first direction to serially engage the second series of teeth 316 of the gear 314. Because the gear 314 and second series of teeth 316 are fixedly coupled to the housing 310, as the first series of teeth 346 moves in the first direction to serially engage the second series of teeth 316, the first series of teeth 346 coupled to or disposed on the second cam 344 correspondingly move (or turn) the second cam from its first position to or towards its second position.

As the second cam 344 moves towards its second position, the first horizontal plane wire 360 is moved in a first direction. Said another way, because the first horizontal plane wire 360 is coupled to the second cam 344, as the second cam moves towards its second position, the second cam pulls on the first horizontal plane wire, and thus moves the first horizontal plane wire in the first direction. Movement of the first horizontal plane wire 360 in the first direction moves (or bends or articulates) the steerable portion 374 of the elongated member 370 in a first direction along the second plane, as illustrated in FIG. 10B.

The second actuator 340 is configured to move the at least a portion of the elongated member 370 along the second plane in a second direction different than the first direction as the second actuator is moved in its second direction, such when the second actuator is moved from its second position to its first position or its third position. As the second actuator 340 is turned in the second direction (indicated by arrow $A_4$ in FIG. 10C) the first series of teeth 346 serially engage the second series of teeth 316 of the gear 314 in an opposite sequence (or order) and the second cam 344 is moved from its second position to or towards its first position. If the user continues moving the second actuator 340 in the second direction after the second cam 344 returns to its first position, the second cam 344 moves to a third position different than the first and second positions.

As the second cam 344 moves to or towards its third position (or to its first position from its second position), the second cam 344 moves the second horizontal plane wire 364 in a first direction. Said another way, because the second cam 344 is coupled to the second horizontal plane wire 364, the second cam pulls the second horizontal plane wire as the second cam moves to or towards its third position. In some embodiments, as the second horizontal plane wire 364 moves in its first direction, the first horizontal plane wire 360 moves in a second direction different than its first direction.

Movement of the second horizontal plane wire 364 in its first direction moves the steerable portion 374 of the elongated member 370 in a second direction different than (or opposite to) the first direction, as illustrated in FIG. 10C. In some embodiments, the second horizontal plane wire 364 is movable in a second direction different than (or opposite to) the first direction, such as when the first horizontal plane wire is moved in its first direction.

In some embodiments, movement of the second actuator 340 and the second cam 344 introduces motion with force leverage directly onto the first horizontal plane wires 360, 364.

Thus, movement of the second actuator 340 controls bi-directional articulation of the elongated member 370 along the second plane. Although the second plane is illustrated and described as being a horizontal plane, in other embodiments, the second plane can be a different plane.

In FIGS. 10B and 10C, the elongated member 370 is illustrated in an articulated position, with the non-articulated (or relaxed) position of the elongated member illustrated in broken lines. The illustrations in FIGS. 10A-10C are representative only, and are not drawn to scale. For example, in some embodiments, the elongated (or steerable) member is a catheter or endoscope of greater length (such as compared to the length of the steering mechanism) than the elongated member in the illustrated embodiments.

Although the steerable medical device 301 is described and illustrated herein as including first and second horizontal plane wires, in other embodiments, the steerable medical device includes a different number of horizontal plane wires. For example, in some embodiments, the steerable medical device includes a single horizontal plane wire. In such an embodiment, the first and second ends of the horizontal plane wire are each coupled to the elongated member of the steerable portion of the device. A portion of the horizontal plane wire between the first end and the second end is coupled to or engaged with the second cam. For example, the horizontal plane wire can extend from its first end coupled to the elongated member through the interior cavity of the housing, a middle portion of the horizontal plane wire can be wrapped around or be coupled to the second cam, and the horizontal plane wire can extend back through the interior cavity of the housing to the second end coupled to the elongated member. In still other embodiments, the steerable medical device includes three, four, or more horizontal plane wires.

Although the horizontal and vertical plane wires are described herein as moving the steerable portion along a substantially horizontal and vertical plane, respectively, in other embodiments, the horizontal and/or vertical plane wires can move the steerable portion along a different plane(s).

The first actuator 330 and second actuator 340 are adapted to be actuated substantially simultaneously. When the first actuator 330 and the second actuator 340 are actuated substantially simultaneously, the elongated member 370 of the steerable medical device 301 is moved along the first plane and the second plane substantially simultaneously. This effectively results in movement of the steerable portion 374 of the device 301 along a third plane that is angular to the first plane and the second plane. For example, in some embodiments, the first plane is a substantially vertical plane and the second plane is a substantially horizontal plane. As the first and second actuators 330, 340 are actuated in unison, the elongated member 370 is moved along a third plane that is different than the vertical and horizontal planes. For example, the third plane can be at a 45 degree angle to the vertical and horizontal planes.

The first actuator 330 is movable with respect to the second actuator 340. The second actuator 340 can be maintained substantially stationary as the first actuator 330 is moved in at least one of the first direction or the second direction. For example, a user can maintain the second actuator 340 substantially stationary as the user moves the lever portion of the first actuator in at least one of the first direction (e.g., towards a first end of the elongate opening 343) and the second direction (e.g., towards a second end of the elongate opening 343).

Although the first actuator 330 is described herein as being at least partially disposed in the second actuator 340, the first actuator 330 and the second actuator 340 are independently actuatable. Said another way, actuation of the first actuator 330 to move the steerable portion of the device along the first plane does not substantially affect or move the position of the steerable portion of the device along the second plane (which is controlled by the second actuator 340).

Similarly, actuation of the second actuator 340 does not substantially affect or move the position of the steerable portion of the device along the first plane (which is controlled by the first actuator 330). As the second actuator 340 is moved in one of its first direction or its second direction, the first cam 332 of the first actuator 330 disposed within the interior cavity 341 of the second actuator correspondingly moves (or rotates) with respect to the longitudinal axis L, but does not move (or "rock") between its first position and its second or third positions, and so does not move the steerable portion 374 of the device 301 along the first plane.

As illustrated in FIGS. 11 and 12, the steering mechanism 300 is adapted for one-handed operation by a user. For example, during an endoscopic procedure, a physician can hold the housing 310 of the steering mechanism 300 in his or her hand while controlling movement of the actuation system 320 with a thumb of the same hand, as shown in FIG. 11. In another example, a physician can hold or rest the housing 310 of the steering mechanism 300 in his or her hand while controlling movement of the actuation system with a finger of the same hand, as shown in FIG. 12.

The actuation system 320 is adapted for one-fingered operation by a user. Said another way, each of the first actuator 330 and the second actuator 340 is adapted to be actuated with a single thumb or finger of the user without requiring the user to reposition the steering mechanism or the user's hand to actuate both the first actuator and the second actuator. User hand positions in addition to those illustrated are also possible to achieve one-handed and/or one-fingered operation of the steering mechanism.

In some embodiments, the steering mechanism 300 of the steerable medical device 301 includes a protrusion 380. For example, in the embodiment illustrated in FIG. 3, the steering mechanism 300 has a protrusion 380 adapted to be coupled to a working channel of an endoscope.

The protrusion 380 includes a first port 382 and a second port 384. As illustrated in FIG. 3, in some embodiments, the second port 384 is orthogonal to the first port 382. In other embodiments, however, the protrusion can include a first port and a second port having a different configuration; for example, a Y-shaped configuration.

The first port 382 can be adapted to receive a medical instrument. For example, in some embodiments, the first port 382 is adapted to receive at least one of a guidewire, laser fiber, stone retrieval basket, biopsy device, or another medical instrument. In a procedure utilizing the steering mechanism 300, a user can insert the medical instrument, such as the guidewire, into the first port 382. The user can continue inserting the guidewire such that the guidewire is received in the working channel of the endoscope.

The second port 384 can be adapted to receive a fluid. For example, the second port 384 can be adapted to receive a fluid for irrigation of the working channel (not shown) of the endoscope. The second port 384 can be adapted to channel or pass the irrigation fluid from a source exterior to the steerable medical device 301 to the working channel defined by the elongated member 370 when the elongated member is coupled to the steering mechanism 300. Said another way, the second port 384 is fluidically coupled to the working channel of the elongated member 370. For example, in some embodiments, the second port 384 can be adapted to allow passage of a fluid that is a liquid, such as saline, a gas, such as an air jet, or a slurry into the working channel of the elongated member 370. In one procedure utilizing the steering mechanism 300, a user can irrigate an area near or surrounding the medical instrument received in the first port 382 of the steering mechanism and/or received in the working channel of the endoscope. For example, the user can introduce a saline solution into the second port 384 while the guidewire is received in the first port 382. In another example, the user can introduce a fluid through second port 384 to irrigate an area within the bodily cavity, such as an area near a treatment site within the bodily cavity.

Although the first port 382 is described as being adapted to receive medical instrumentation, in other embodiments, the first port is adapted to receive an irrigation fluid. Although the second port 384 is illustrated and described as being adapted to receive an irrigation fluid, in other embodiments, the second port is adapted to receive a medical instrumentation.

Additionally, although the steering mechanism 300 of the steerable medical device 301 is illustrated and described as including a protrusion 380 that has a first port 382 and a second port 384, in other embodiments, the steering mechanism includes a protrusion having no port, a single port, or a plurality of ports, such as three or more ports.

The protrusion 380 is disposed on or coupled to the housing 310 of the steering mechanism 300. For example, in some embodiments, the protrusion 380 is monolithically constructed with the housing 310. In other embodiments, the protrusion 380 is separately constructed and then coupled to the housing 310. In the illustrated embodiment, the protrusion 380 is coupled to the distal end 313 of the housing 310. In other embodiments, the protrusion 380 can be coupled to a different portion of the steerable medical device 301.

In a procedure utilizing a steering mechanism according to the present invention, the user can hold or rest the housing in one of the user's hands, or rest the housing on a preferred location. The user places a thumb or finger onto the first actuator. To move the steerable member or portion of the medical device in a vertical direction, the user pulls, pushes, or otherwise moves the first actuator. To move the steerable member or portion in a horizontal direction, the user turns or otherwise moves the second actuator to the right or to the left (or clockwise or counterclockwise) from the perspective of the user. The user can substantially simultaneously move both the first actuator and the second actuator to move the steerable member or portion in a direction other than a vertical or horizontal direction. For example, the user can substantially simultaneously push the first actuator towards a distal end of the device and turn the second actuator to the right to move the steerable member or portion at a 45 degree angle. The user can also achieve articulation of the steerable member or portion at the 45 degree (or other) angle by sequentially moving the first actuator and the second actuator. The steering mechanism is configured such that the user can control articulation of the steerable member or portion in substantially any angle or direction that is 360 degrees about the longitudinal axis L.

While various embodiments of the invention have been described above, it should be understood that they have been presented by way of example only, and not limitation. For example, although the steering mechanism 300 is described herein as including a gear 314 and two series of engaging teeth 316, 346, in other embodiments, the steering mechanism incorporates a different type of gear system or arrangement. Thus, the breadth and scope of the invention should not be limited by any of the above-described embodiments, but should be defined only in accordance with the claims and their equivalents.

What is claimed is:

1. A steering mechanism for use as part of a medical device, comprising:
   a housing including a proximal end and a distal end, the housing couplable to a steerable medical device, the housing substantially extending along a longitudinal axis; and
   an actuation system adapted for one-handed operation by a user, the actuation system configured to move at least a portion of the steerable medical device along a first plane and a second plane different than the first plane such that 360 degree articulation of the steerable medical device is achievable, the actuation system including a first actuator and a second actuator, the first actuator movable with respect to the second actuator along the longitudinal axis and about a second axis different than the longitudinal axis, the first actuator at least partially disposed within the second actuator, the second actuator coupled to the proximal end of the housing, the second actuator movable with respect to the housing and about the longitudinal axis.

2. The steering mechanism of claim 1, wherein the first actuator and the second actuator are adapted for one-fingered operation by a user.

3. The steering mechanism of claim 1, wherein the first actuator is movable in a first direction and a second direction different than the first direction, the first actuator configured to move the at least a portion of the steerable medical device in a first direction and a second direction different than the first direction along the first plane as the first actuator is moved in its first direction and its second direction, respectively.

4. The steering mechanism of claim 1, wherein the second actuator is movable in a first direction and a second direction different than the first direction, the second actuator configured to move the at least a portion of the steerable medical device in a first direction and a second direction different than the first direction along the second plane as the second actuator is moved in its first direction and its second direction, respectively.

5. The steering mechanism of claim 1, wherein the second actuator includes a casing defining an interior cavity adapted to receive at least a portion of the first actuator.

6. The steering mechanism of claim 5, wherein the first actuator includes a cam at least partially disposed within the interior cavity of the casing of the second actuator.

7. The steering mechanism of claim 6, wherein the first actuator includes a lever portion configured to extend from the cam at least partially disposed within the casing of the second actuator through an elongate opening defined by the casing of the second actuator.

8. The steering mechanism of claim 6, wherein the cam of the first actuator is a first cam, the second actuator including a second cam at least partially disposed within the interior cavity of the casing of the second actuator.

9. The steering mechanism of claim 1, wherein the first actuator is movably coupled to the second actuator by a dowel pin.

10. The steering mechanism of claim 1, wherein the second actuator includes a cam configured to move a horizontal plane wire when the second actuator is moved in at least one of its first direction and its second direction.

11. The steering mechanism of claim 1, further comprising:
    a gear fixedly coupled to the housing, the gear adapted to engage a portion of the second actuator as the second actuator is moved in at least one of the first direction and the second direction; and
    a cam included in the second actuator and movable between a first position and a second position different than the first position, the cam configured to move from its first position towards its second position as the second actuator is moved in its first direction and as the portion of the second actuator engages the gear.

12. The steering mechanism of claim 11, wherein the portion of the second actuator includes a first series of teeth in a circular configuration, the gear including a second series of teeth configured to matingly engage the first series of teeth of the portion of the second actuator as the second actuator is moved in at least one of its first direction and its second direction.

13. A steerable medical device, comprising:
    an elongated member including a proximal end and a distal end and a lumen extending at least partially therethrough, the elongated member including a steerable portion, the elongated member extending along a longitudinal axis when the elongated member is in a first position; and
    a steering mechanism coupled to the elongated member, the steering mechanism adapted to move the steerable portion of the elongated member along at least a first plane and a second plane different than the first plane, the steering mechanism adapted for one-handed operation by a user, the steering mechanism including:
        a first actuator adapted to move the steerable portion of the elongated member along the first plane; and
        a second actuator adapted to move the steerable portion of the elongated member along the second plane, the first actuator movably coupled to and at least partially extending into the second actuator, wherein the first actuator is movable with respect to the second actuator along the longitudinal axis and the second actuator is movable about the longitudinal axis.

14. The steerable medical device of claim 13, wherein the steering mechanism is adapted to achieve 360 degree articulation of the steerable portion of the elongated member with respect to the longitudinal axis.

15. The steerable medical device of claim 13, the steering mechanism further comprising:
a housing including a proximal end and a distal end and defining an interior cavity extending at least partially therethrough, the distal end of the housing coupled to the proximal end of the elongated member, the second actuator movably coupled to the proximal end of the housing.

16. The steerable medical device of claim 15, the second actuator selectively turnable in a first direction and a second direction different than the first direction around the longitudinal axis and with respect to the housing.

17. The steerable medical device of claim 15, further comprising:
a gear fixedly coupled to the housing, the gear adapted to engage a portion of the second actuator as the second actuator is actuated; and
a cam included in the second actuator and configured to move between a first position and a second position as the second actuator is actuated and as the portion of the second actuator engages the gear.

18. The steerable medical device of claim 13, further comprising:
a wire coupled to the elongated member and to the first actuator, the wire movable in a first direction and a second direction different than the first direction, wherein, when the first actuator is moved in its first direction, the wire moves in its first direction, and wherein the wire is configured to move the steerable portion of the elongated member in the first direction along the first plane when the wire moves in its first direction.

19. The steerable medical device of claim 13, further comprising:
a wire coupled to the elongated member and to the second actuator, the wire movable in a first direction and a second direction different than the first direction, wherein, when the second actuator is moved in its first direction, the wire moves in its first direction, and wherein the wire is configured to move the steerable portion of the elongated member in the first direction along the second plane when the wire moves in its first direction.

20. The steerable medical device of claim 13, wherein the first actuator is at least partially disposed within a casing of the second actuator.

* * * * *